(12) United States Patent
Itakura et al.

(10) Patent No.: US 7,481,107 B2
(45) Date of Patent: Jan. 27, 2009

(54) HUMIDITY SENSOR WITH SETTING MEMBER FOR SETTING MAXIMUM AMOUNT OF MOISTURE IN HUMIDITY SENSITIVE MEMBER

(75) Inventors: Toshikazu Itakura, Toyota (JP); Toshiki Isogai, Nagoya (JP)

(73) Assignees: DENSO CORPORATION, Kariya (JP); NIPPON SOKEN, INC., Nishio (JP)

( * ) Notice: Subject to any disclaimer, the term of this patent is extended or adjusted under 35 U.S.C. 154(b) by 22 days.

(21) Appl. No.: 11/633,450

(22) Filed: Dec. 5, 2006

(65) Prior Publication Data

US 2007/0131020 A1    Jun. 14, 2007

(30) Foreign Application Priority Data

Dec. 8, 2005    (JP)    ............................. 2005-354820
Nov. 6, 2006    (JP)    ............................. 2006-300087

(51) Int. Cl.
    *H02H 3/00*    (2006.01)
(52) U.S. Cl. ................................. 73/335.02; 73/335.04
(58) Field of Classification Search .............. 73/335.02, 73/335.04
    See application file for complete search history.

(56) References Cited

U.S. PATENT DOCUMENTS

| | | | | |
|---|---|---|---|---|
| 2,768,629 | A | * | 10/1956 | Maul ........................... 131/303 |
| 5,296,819 | A | * | 3/1994 | Kuroiwa et al. ............. 324/670 |
| 5,578,753 | A | * | 11/1996 | Weiss et al. ............... 73/335.02 |
| 6,356,087 | B1 | | 3/2002 | Wallrafen |
| 6,450,026 | B1 | * | 9/2002 | Desarnaud ............... 73/335.04 |
| 2004/0177685 | A1 | * | 9/2004 | Yokura et al. ............ 73/335.04 |
| 2005/0028588 | A1 | * | 2/2005 | Mitter ....................... 73/335.04 |
| 2006/0186901 | A1 | | 8/2006 | Itakura et al. |
| 2006/0194332 | A1 | | 8/2006 | Wado et al. |

FOREIGN PATENT DOCUMENTS

| | | |
|---|---|---|
| JP | A-62-019746 | 1/1987 |
| JP | A-02-140654 | 5/1990 |
| JP | A-2002-156348 | 5/2002 |

OTHER PUBLICATIONS

Office Action dated Jul. 4, 2008 in corresponding German patent application No. 10 2006 05 7945.3-52 (and English translation).

* cited by examiner

*Primary Examiner*—Michael Cygan
(74) *Attorney, Agent, or Firm*—Posz Law Group, PLC (57) ABSTRACT

A humidity sensor includes: a substrate; a pair of electrodes on the substrate; a humidity sensitive member between the electrodes having a capacitance changeable in accordance with humidity; an output element connecting to the electrodes in order to detect a capacitance of the humidity sensitive member and outputting a signal corresponding to the capacitance; and a setting member for setting a maximum amount of moisture in the humidity sensitive member to be a standard maximum amount of moisture. The humidity sensitive member is capable of absorbing a moisture up to the maximum amount of moisture. The setting member includes at least one of an element for reducing the maximum amount of moisture and an element for increasing the maximum amount of moisture.

13 Claims, 4 Drawing Sheets

HUMIDITY SENSOR WITH SETTING MEMBER FOR SETTING MAXIMUM AMOUNT OF MOISTURE IN HUMIDITY SENSITIVE MEMBER

CROSS REFERENCE TO RELATED APPLICATIONS

This application is based on Japanese Patent Applications No. 2005-354820 filed on Dec. 8, 2005, and No. 2006-300087 filed on Nov. 6, 2006, the disclosures of which are incorporated herein by reference.

FIELD OF THE INVENTION

The present invention relates to a humidity sensor with a setting member for setting a maximum amount of moisture in a humidity sensitive member.

BACKGROUND OF THE INVENTION

A humidity sensor for detecting humidity in atmosphere is disclosed in, for example, JP-A-H02-140654. This sensor includes a humidity sensitive film made of high-polymer material having moisture-absorption characteristics. The humidity sensitive film has multiple fine pores, dimensions of which are about a few nanometers. The moisture is absorbed in the fine pores, and desorbed from the fine pores. In accordance with absorption and desorption of the moisture, dielectric constant of the humidity sensitive film is changed. In general, the dielectric constant of the moisture is larger than that of the high-polymer material. Accordingly, when the humidity sensitive film absorbs the moisture, the dielectric constant of the film becomes larger. By detecting a capacitance of the humidity sensitive film, the humidity in atmosphere is detected.

Figure 6A:
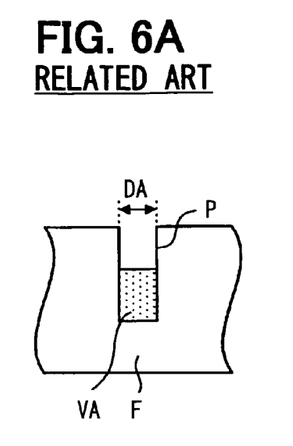
Figure 6B:
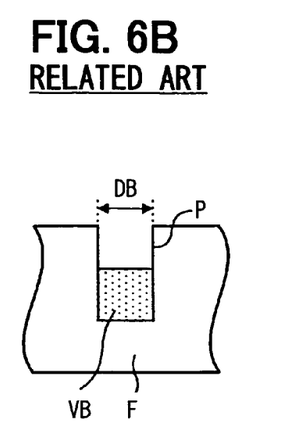
Figure 6C:
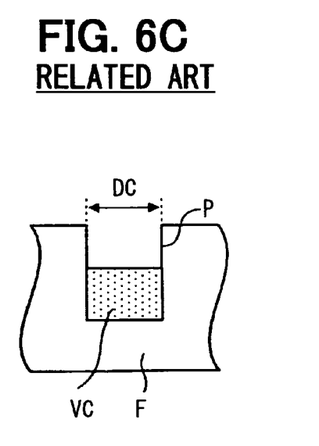
Figure 6D:
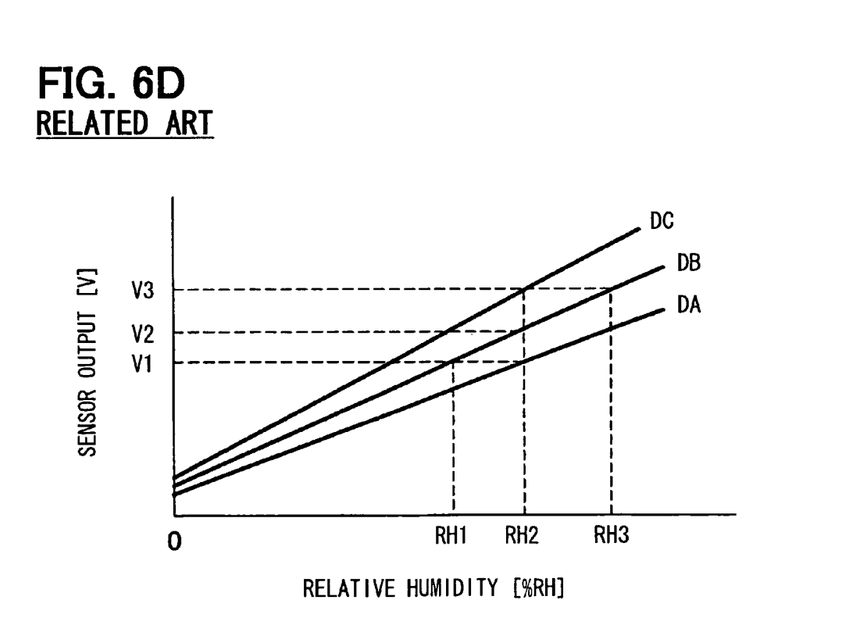
FIG. 6D is a graph showing sensor characteristics of the sensor in FIGS. 6A to 6C, according to a related art.

FIGS. 6A to 6D shows sensor characteristics of the humidity sensor with reference to maximum amount of moisture in the humidity sensitive film. Here, the maximum amount of moisture is defined such that the humidity sensitive film F is capable of absorbing the moisture equal to or smaller than the maximum amount of moisture. FIGS. 6A to 6C are cross sectional views explaining change of maximum amount of moisture in the humidity sensitive film in accordance with humidity change. FIG. 6D shows sensor characteristics of the humidity sensor in each humidity condition. Here, the sensor characteristics relate to a relationship between a sensor output and a relative humidity in atmosphere. In this sensor, when the sensor is manufactured, the sensor characteristics are set to be a graph DB in FIG. 6B. FIG. 6A shows the sensor when the humidity is comparatively low, and FIG. 6C shows the sensor when the humidity is comparatively high. When the humidity becomes higher, the film F swells, and therefore, the sensor changes from a state in FIG. 6B to a state in FIG. 6C. When the humidity becomes lower, the film F shrinks, and therefore, the sensor changes from a state in FIG. 6B to a state in FIG. 6A.

When the sensor is just manufactured, the diameter of the fine pore P in the humidity sensitive film F is defined as DB, and the maximum amount of moisture in the film F is defined as VB. When the sensor is maintained in a comparatively high humidity condition, the film F swells in accordance with absorption of moisture. In this case, the diameter of the fine pore P changes from DB to DC. Thus, the average of diameter distribution of the fine pores P becomes larger. In this case, the maximum amount of moisture in the film F increases from VB to VC. Thus, the moisture in the atmosphere is easily absorbed in the film F. As a result, even when the humidity is the same, the capacitance change of the film F becomes larger. Thus, as shown in FIG. 6D, the sensor output becomes larger, so that the sensor characteristics changes from DB to DC. Specifically, the sensitivity of the sensor with reference to the humidity becomes larger.

In this case, the following problems occur. For example, when the humidity in the atmosphere is RH2 in FIG. 6D, the sensor output is V2 in a case where the sensor has the sensor characteristics DB, which is the initial sensor characteristics. However, the maximum amount of moisture in the film F increases, so that the sensor characteristics of the sensor change to the characteristics DC. Thus, the output of the sensor changes from V2 to V3. In this case, since the sensor characteristics are set to be DB, the humidity sensor calculates the humidity as RH3, which corresponds to the output V3. Although the actual humidity is RH2, the detected humidity is RH3, which is higher than the actual humidity.

When the sensor is maintained in a comparatively low humidity condition, as shown in FIG. 6A, the moisture is desorbed from the film F. In this case, the diameter of the fine pore P changes from DB to DA. Thus, the average of diameter distribution of the fine pores P becomes smaller. In this case, the maximum amount of moisture in the film F decreases from VB to VA. Thus, the moisture in the atmosphere is not easily absorbed in the film F. As a result, even when the humidity is the same, the capacitance change of the film F becomes smaller. Thus, as shown in FIG. 6D, the sensor output becomes smaller, so that the sensor characteristics changes from DB to DA. Specifically, the sensitivity of the sensor with reference to the humidity becomes smaller.

In this case, the following problems occur. For example, when the humidity in the atmosphere is RH2 in FIG. 6D, the sensor output is V2 in a case where the sensor has the sensor characteristics DB, which is the initial sensor characteristics. However, the maximum amount of moisture in the film F increases, so that the sensor characteristics of the sensor change to the characteristics DA. Thus, the output of the sensor changes from V2 to V1. In this case, since the sensor characteristics are set to be DB, the humidity sensor calculates the humidity as RH1, which corresponds to the output V1. Although the actual humidity is RH2, the detected humidity is RH1, which is lower than the actual humidity.

Thus, the sensor characteristics changes in accordance with environment of the sensor disposed before humidity detection. Accordingly, detection error may be observed.

SUMMARY OF THE INVENTION

In view of the above-described problem, it is an object of the present disclosure to provide a humidity sensor.

According to an aspect of the present disclosure, a humidity sensor includes: a substrate; a pair of electrodes arranged on the substrate in such a manner that the electrodes are separated each other by a predetermined distance therebetween; a humidity sensitive member disposed between the electrodes, wherein the humidity sensitive member has a capacitance, which is changeable in accordance with humidity; an output element connecting to the electrodes in order to detect a capacitance of the humidity sensitive member and outputting a signal corresponding to the capacitance; and a setting member for setting a maximum amount of moisture in the humidity sensitive member to be a standard maximum amount of moisture. The humidity sensitive member is capable of absorbing a moisture up to the maximum amount of moisture. The setting member includes at least one of an element for reducing the maximum amount of moisture and an element for increasing the maximum amount of moisture.

In the above sensor, before detection of the humidity, the sensor characteristics reproducibly return to the standard characteristics so that detection accuracy of the sensor is improved.

BRIEF DESCRIPTION OF THE DRAWINGS

The above and other objects, features and advantages of the present invention will become more apparent from the following detailed description made with reference to the accompanying drawings. In the drawings:

FIG. 6A is a cross sectional view showing a humidity sensor under a low humidity condition, FIG. 6B is a cross sectional view showing the sensor at a manufacturing time, FIG. 6C is a cross sectional view showing the sensor under a high humidity condition.

DETAILED DESCRIPTION OF THE PREFERRED EMBODIMENTS

First Embodiment

Figure 1:
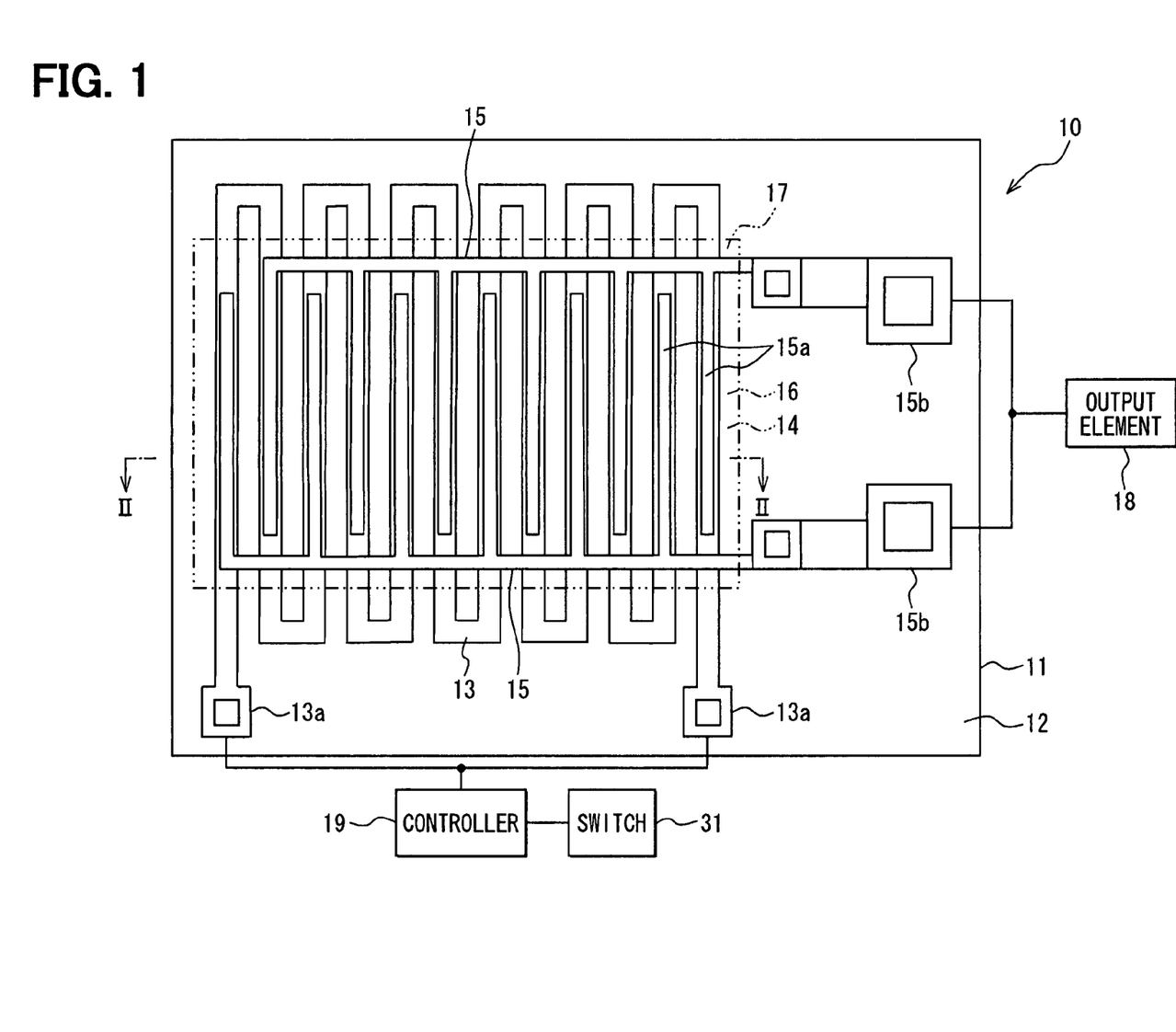
FIG. 1 is a plan view showing a humidity sensor.
Figure 2:
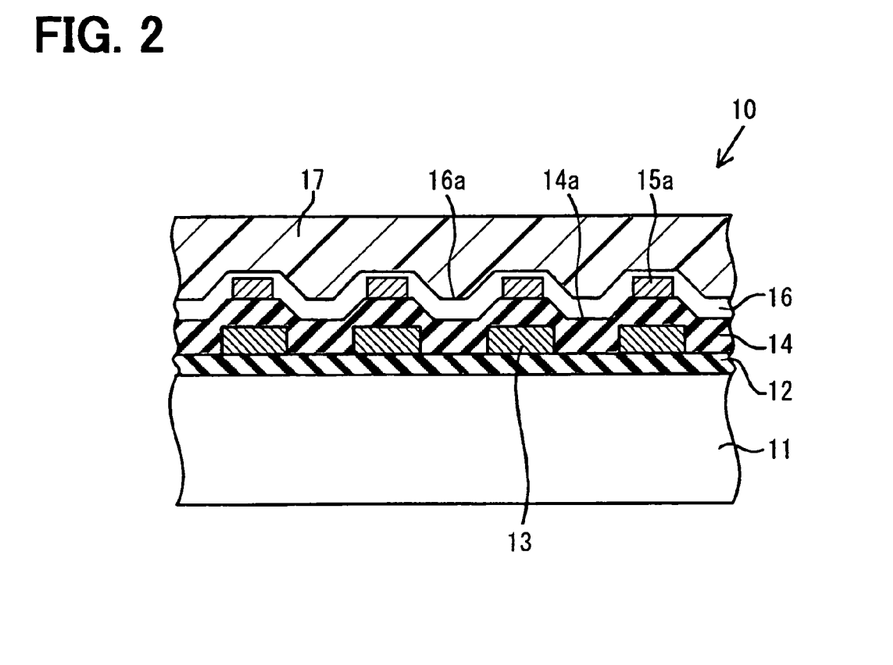
FIG. 2 is a cross sectional view showing the sensor taken along line II-II in FIG. 1.
Figure 3:
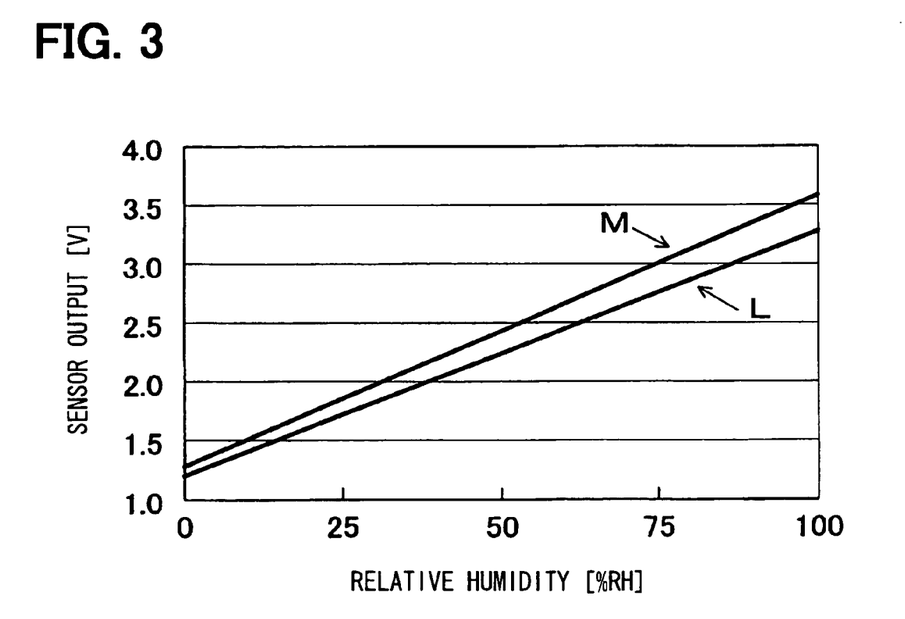
FIG. 3 is a graph showing sensor characteristics of the sensor in FIG. 1.

A humidity sensor 10 is shown in FIGS. 1-3. The sensor 10 includes a first insulation film 12, a heater 13, a second insulation film 14, a detection electrode 15, a protection film 16 and a humidity sensitive film 17, which are stacked on a substrate 11 in this order.

The heater 13 is electrically connected to a heater controller 19 through a heater electrode pad 13a. The heater controller 19 is electrically connected to a starter switch 31 of, for example, an automotive vehicle. The detection electrode 15 is electrically connected to an output element 18 through an electrode pad 15b. The output element 18 outputs a voltage signal corresponding to a detected capacitance of the humidity sensitive film 17.

The substrate 11 is made of semiconductor material such as silicon. The first insulation film 12 is formed on one side of the substrate 11. The first insulation film 12 is made of silicon oxide. The heater 13 is formed on the first insulation film 12. The heater 13 is made of, for example, a poly silicon thin film. The first insulation film 12 has a meander shape having a predetermined width. The width of the first insulation film 12 is almost the same as a comb-teeth portion 15a of the detection electrode 15. The first insulation film 12 is disposed under the comb-teeth portion 15a of the detection electrode 15.

The second insulation film 14 is formed by, for example, a plasma CVD method to cover the heater 13 and the first insulation film 12. The second insulation film 14 is made of silicon oxide. Here, the thickness of the second insulation film 14 is homogeneous over the heater 13 and the second insulation film 14. Accordingly, a concavity 14a is formed between neighboring rows of the heater 13.

The detection electrode 15 includes a pair of comb-teeth portions 15a, which face each other and are disposed on the second insulation film 14. The detection electrode 15 is formed such that an aluminum film is deposited on the second insulation film 14 by using, for example, a sputtering method. Then, the aluminum film is patterned to have a comb-teeth pattern on the heater 13 so that the detection electrode 15 is completed. The comb-teeth portions 15a are interleaved. Specifically, one of the comb-teeth portion 15a is disposed between the other one of the comb-teeth portion 15a. The detection electrode 15 may be made of low resistance metallic material such as copper, gold and platinum.

The protection film 16 is formed on the second insulation film 14 to cover the detection electrode 15 so that the protection film 16 protects the detection electrode 15 from erosion of the moisture. The protection film 16 is made of a silicon nitride film, which is formed by, for example, a plasma CVD method. The thickness of the protection film 16 is homogeneous to cover the second insulation film 14. Thus, a concavity 16a is formed between the comb-teeth portions 15a.

The humidity sensitive film 17 is formed on the protection film 16. The capacitance of the humidity sensitive film 17 is changeable in accordance with the humidity in atmosphere. The humidity sensitive film 17 covers the detection electrode 15 and a clearance between the comb-teeth portions 15a of the detection electrode 15. The humidity sensitive film 17 is formed such that a poly imide resin film is applied on the protection film 16 by using a spin coating method, a printing method or the like. Then, the poly imide resin film is heated at a predetermined temperature so that the poly imide resin film is hardened. Thus, the poly imide resin film has the thickness about a few microns. The humidity sensitive film 17 has multiple fine pores having dimension of a few nanometers. The fine pore is capable of absorbing the moisture in the atmosphere and desorbing the moisture in the pore to the atmosphere, so that the dielectric constant of the humidity sensitive film 17 is changed. The dielectric constant of the moisture is larger than that of the poly imide resin film. Accordingly, the dielectric constant of the humidity sensitive film 17 becomes larger in accordance with the moisture absorbed in the fine pores when the humidity sensitive film 17 absorbs the moisture in accordance with the humidity in the atmosphere. Thus, the capacitance of a capacitor provided by the detection electrode 15 and the humidity sensitive film 17 between the comb-teeth portions 15a is changed. The capacitance is measured by the output element 18, and a voltage signal corresponding to the capacitance is outputted from the output element 18. On the basis of the voltage signal and the sensor characteristics of the sensor 10, the humidity in the atmosphere is detected.

Since the detection electrode 15 has the comb-teeth pattern, a total facing area of the comb-teeth portions 15a becomes large although a planar area of the detection electrode 15 is small. Thus, the capacitance change of the capacitor in accordance with the humidity change in the atmosphere becomes larger, so that the sensitivity of the sensor 10 is improved.

Further, the concavity 16a is formed on the protection film 16, so that the amount of the humidity sensitive film 17 disposed between the comb-teeth portions 15a increases. Accordingly, the sensitivity of the sensor 10 is improved, compared with a case where the heater 13 is not disposed under the comb-teeth portions 15a and the sensor 10 has no concavity 16a between the comb-teeth portions 15a.

FIG. 3 shows variation of the sensor characteristics of the sensor 10 with reference to the maximum amount of moisture in the humidity sensitive film 17. Here, the maximum amount of moisture is defined such that the humidity sensitive film 17 is capable of absorbing the moisture equal to or smaller than the maximum amount of moisture. In FIG. 3, for example, a curve M represents the sensor characteristics when the sensor 10 is just manufactured, i.e., the curve M is the initial sensor characteristics at a manufacturing time. Here, the sensor characteristics are a relationship between the humidity change, i.e., the relative humidity change and the output of the sensor 10.

When the sensor 10 is displaced in a certain environment having certain humidity, which is different from the initial environmental humidity, the sensor characteristics are changed from the initial characteristics M to other characteristics. Thus, the maximum amount of moisture is changed from the initial maximum amount to certain maximum amount, i.e., the average of the diameter of the fine pores in the humidity sensitive film 17 is changed from the initial diameter to a certain diameter. Accordingly, in a conventional sensor, the sensor outputs the signal corresponding to the humidity based on the changed characteristics, and the humidity is detected by using the signal and the initial characteristics M, so that the detection error of the humidity may be observed. In view of this difficulty, before the sensor detects the humidity, the changed characteristics of the sensor 10 are returned to the initial characteristics M. To realize this return, it is necessary to set the initial characteristics M to easily repeatable sensor characteristics.

In this embodiment, when the initial characteristics of the sensor 10 is set just after the sensor is manufactured, the initial maximum amount of moisture in the humidity sensitive film 17 is set to be a lower limit of the maximum amount of moisture or to be a value near the lower limit. Next, the output of the sensor 10 is detected along with changing the humidity. Thus, the standard sensor characteristics L in FIG. 3 is obtained and memorized in the output element 18 on the basis of the relationship between the humidity and the output. Here, when the humidity sensitive film 17 is maintained under the low humidity condition, the average of the fine pores in the humidity sensitive film 17 becomes smaller so that the amount of moisture in the fine pores is reduced. Thus, the output of the sensor 10 is also reduced, and the sensitivity with reference to the humidity is reduced. Thus, the sensor characteristics are changed from the initial characteristics M to the standard characteristics L.

For example, the sensor 10 is maintained under a predetermined condition for a predetermined time by using a constant temperature chamber or the like. Here, the condition is, for example, such that the temperature is 85° C., the humidity is equal to or lower than 10% RH, and the predetermined time is, for example, 200 hours. In this case, the maximum amount of moisture in the humidity sensitive film 17 becomes the lower limit or approximately lower limit. This condition is defined as the standard condition. Then, the standard sensor characteristics L are measured and set based on a relationship between the humidity and the output of the sensor 10. When the maximum amount of moisture in the humidity sensitive film 17 is the lower limit of the maximum amount of moisture, the average of diameter of the fine pores in the film 17 is minimized, so that the standard characteristics L shows the lower limit of sensitivity with reference to the humidity.

Thus, the standard characteristics L are set to be the lower limit of maximum amount of moisture. In this case, when the sensor detects the humidity, the moisture is removed as much as possible before detection of the humidity. The sensor characteristics become the standard characteristics L. After that, the humidity is detected by the sensor 10 with the standard sensor characteristics L. In this case, the humidity is accurately and with high-reproducibility detected.

Here, the humidity sensitive film 17 may be heated by the heater 13 just after the sensor 10 is manufactured so that the maximum amount of moisture in the humidity sensitive film 17 becomes the lower limit, i.e., the sensor characteristics becomes the standard characteristics L. In this case, it is not necessary for the sensor to maintain under the predetermined condition by using the constant temperature chamber. Specifically, the standard characteristics L are set without using the constant temperature chamber or the like.

Before the sensor 10 detects the humidity, the sensor characteristics are returned to the standard characteristics L. For example, in a case where the sensor 10 is mounted on an automotive vehicle, the humidity sensitive film 17 is heated at around 100° C. for 30 minutes by energizing the heater 13 through the heater controller 19 when a driver turns on the start switch 31 such as an ignition switch. Thus, the maximum amount of moisture in the humidity sensitive film 17 is returned to the lower limit or approximately lower limit, i.e., the sensor characteristics are returned to the standard characteristics L.

Thus, just after the start switch 31 turns on, the sensor characteristics are changed to the standard characteristics L within a short time. Thus, on the basis of the standard characteristics L, which is initially set, the sensor 10 detects the humidity.

Accordingly, even when the humidity sensitive film 17 preliminarily absorbs the moisture, the sensor characteristics are returned to the standard characteristics L. Thus, the sensor characteristics are highly reproducible so that the sensor 10 detects the humidity with high accuracy. Specifically, the influence of deviation of the sensor characteristics from the initial characteristics M is eliminated.

In a case where the driver drives the vehicle at frequent intervals, the humidity sensitive film 17 may be heated by energizing the heater so that the sensor characteristics are set to be the standard characteristics L when the start switch 31 of the vehicle is turned off. In this case, it is not required to prepare the sensor 10 for detecting the humidity immediately. Accordingly, the heating condition may be relaxed. For example, the heating condition is such that the heating temperature is 65° C., and the heating time is about 5 minutes.

Alternatively, the humidity sensitive film 17 may be heated at a certain timing other than a switch-on operation and a switch-off operation of the vehicle. For example, when an interval between the latest switch-off operation and the successive switch-on operation is within 6 hours, the heater is not energized even when the start switch 31 turns on.

Alternatively, the driver or a passenger of the vehicle may operate a switch for the heater 13. In this case, for example, the driver switches on the heater 13 before the vehicle runs so that the humidity sensitive film 17 is heated.

Alternatively, the heater 13 may be always energized so that the humidity sensitive film 17 is heated. Only when the humidity is detected by the sensor, the heater 13 stops to heat the humidity sensitive film 17. Then, the humidity is detected.

Alternatively, the humidity sensitive film 17 may be heated during the vehicle runs. In this case, the output of the humidity sensor 10 is not used for another system such as an air conditioning system. For example, the humidity sensitive film 17 can be heated during the vehicle runs when the temperature of a passenger's compartment is detected around 40° C. by an inner air sensor, when a solar radiation sensor detects amount of solar radiation equal to or larger than a predetermined amount, or when a ECU determines that there is no need to use the output of the humidity sensor 10 in another system in a case where information about weather and/or season is obtained by a GPS information system or other communication systems. In this case, the heater 13 does not heat the humidity sensitive film 17 until the sensor detects the humidity. Specifically, just before the sensor detects the humidity, the humidity sensitive film 17 is heated. Thus, the sensitivity of the sensor 10 is improved.

Alternatively, the heater 13 may be operated on the basis of the temperature in the compartment of the vehicle, the temperature detected by a compartment air temperature sensor.

For example, in winter, the temperature of the compartment is, for example, equal to or lower than 10° C. In such a low temperature and low humidity condition, the sensor characteristics are substantially not varied. Thus, there is no need to operate the heater 13. Further, in summer, the temperature of the compartment is, for example, equal to or higher than 40° C. In this case, an air conditioning system always functions, so that there is no need to use the output of the humidity sensor 10 for control of the air conditioning system. Thus, the heater 13 is operated so that the sensor characteristics are returned.

Thus, for example, the heater 13 is operated and/or stops to heat the humidity sensitive film 17 on the basis of the temperature of the compartment. Thus, since the heater 13 is operated only in case of necessity, energy consumption of the heater 13 is reduced. Here, the above temperature conditions are not limited to 10° C. and 40° C.

The substrate 11 may be made of an insulation substrate such as a glass substrate and a resin substrate. When the detection electrode 15 is not eroded or deteriorated by environment, the sensor 10 may not have the protection film 16. Further, the detection electrode 15 may not have the comb-teeth pattern. Alternatively, the detection electrode 15 may have a construction such that a pair of plate electrodes faces each other. The heater 13 may not be disposed on the first insulation film 12. Alternatively, an insulation film may be formed on a backside of the substrate 11, and the heater 13 is formed on the backside of the substrate through the insulation film. Further, the heater 13 may be formed on the humidity sensitive film 17. The sensor 10 may have another construction as long as the humidity sensitive film 17 is formed between the comb-teeth portions 15a.

In the above sensor 10, the moisture absorbed in the humidity sensitive film 17 is evaporated by using the heater 13, so that the maximum amount of moisture in the humidity sensitive film 17 is set to be the lower limit or approximately lower limit of the maximum amount of moisture, which is initially set as the standard characteristics.

Accordingly, before detection of the humidity, the sensor has the standard characteristics L with high reproducibility. Thus, the influence of deviation of the sensor characteristics from the initial characteristics M is eliminated. Further, the detection accuracy of the humidity is improved.

The sensor characteristics are reset to be the standard characteristics L when the start switch 31 of the vehicle turns on. Thus, before the humidity in the passenger compartment is detected, the sensor characteristics are reset to be the standard characteristics L with high reproducibility. Thus, the influence of deviation of the sensor characteristics from the initial characteristics M is eliminated. Further, the detection accuracy of the humidity is improved. Accordingly, the humidity data for controlling various system of the vehicle and for controlling various conditions such as humidity in the vehicle is accurately detected, so that the driver and the passenger in the vehicle can drive the vehicle comfortably.

Since the humidity sensitive film 17 is made of poly imide resin, the heater 13 can heat the humidity sensitive film 17 up to a comparative high temperature. This is because the poly imide resin material has high temperature resistance. Thus, the moisture in the humidity sensitive film 17 can be evaporated within a comparative short time.

Since the comb-teeth portion 15a are interleaved, the total facing area of the comb-teeth portions 15a is maximized. Further, the concavity 16a is formed between the comb-teeth portions 15a, so that the volume of the humidity sensitive film 17 disposed between the comb-teeth portions 15a becomes larger. Thus, the capacitance change in accordance with humidity change is maximized, so that the sensitivity of the sensor 10 is improved.

Second Embodiment

Figure 4:
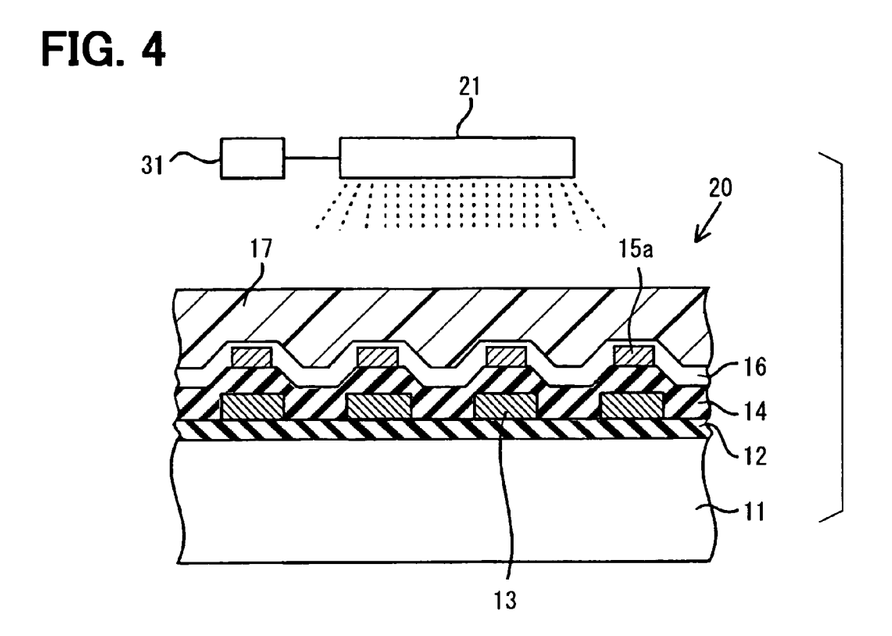
FIG. 4 is a cross sectional view showing another humidity sensor.
Figure 5:
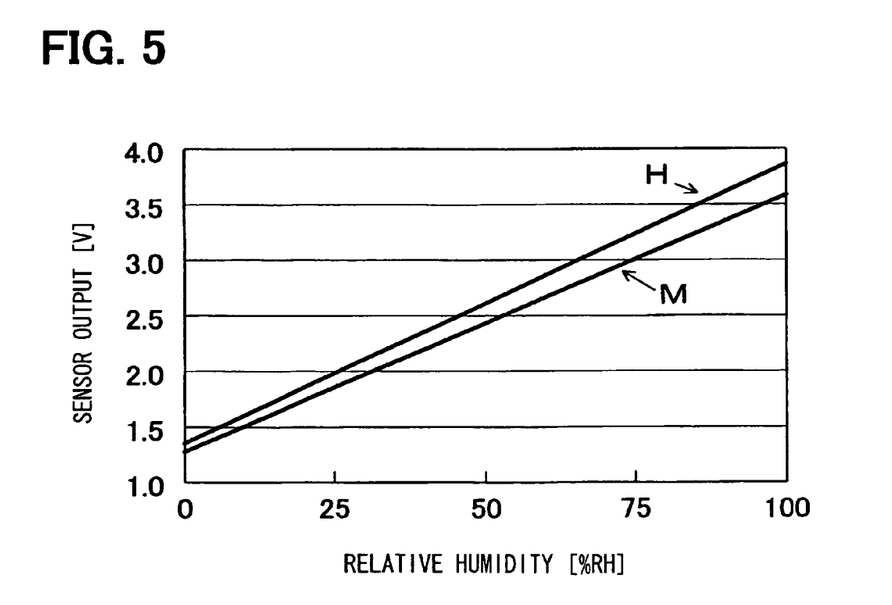
FIG. 5 is a graph showing sensor characteristics of the sensor in FIG. 4.

FIG. 4 shows a humidity sensor according to a second embodiment. FIG. 5 shows variation of the sensor characteristics of the sensor 10 with reference to the maximum amount of moisture in the humidity sensitive film 17.

The sensor 10 includes a moisture supply element 21 for supplying the moisture to the humidity sensitive film 17. The moisture supplying element 21 supplies high temperature and high humidity atmosphere to the humidity sensitive film 17 by using emission gas, which is returned to an engine compartment.

In this embodiment, when the initial characteristics of the sensor 10 are set just after the sensor is manufactured, the initial maximum amount of moisture in the humidity sensitive film 17 is set to be an upper limit of the maximum amount of moisture or to be a value near the upper limit. Next, the output of the sensor 10 is detected along with changing the humidity. Thus, the standard sensor characteristics H in FIG. 5 is obtained and memorized in the output element 18 on the basis of the relationship between the humidity and the output. Here, when the humidity sensitive film 17 is maintained under the high humidity condition, the average of the fine pores in the humidity sensitive film 17 becomes larger so that the amount of moisture in the fine pores is increased. Thus, the output of the sensor 10 is also increased, and the sensitivity with reference to the humidity is increased. Thus, the sensor characteristics are changed from the initial characteristics M to the standard characteristics H.

For example, the sensor 10 is maintained under a predetermined condition for a predetermined time by using a constant temperature chamber or the like. Here, the condition is, for example, such that the temperature is 85° C., the humidity is equal to 90% RH, and the predetermined time is, for example, 200 hours. In this case, the maximum amount of moisture in the humidity sensitive film 17 becomes the upper limit or approximately upper limit. This condition is defined as the standard condition. Then, the standard sensor characteristics H are measured and set based on the humidity and the output of the sensor 10. When the maximum amount of moisture in the humidity sensitive film 17 is the upper limit of the maximum amount of moisture, the average of diameter of the fine pores in the film 17 is maximized, so that the standard characteristics H shows the upper limit of sensitivity with reference to the humidity.

Thus, the standard characteristics H are set to be the upper limit of maximum amount of moisture. In this case, when the sensor detects the humidity, the moisture is removed as much as possible before detection of the humidity. The sensor characteristics become the standard characteristics H. After that, the humidity is detected by the sensor 10 with the standard sensor characteristics H. In this case, the humidity is accurately and with high-reproducibility detected.

Here, the moisture may be added into the humidity sensitive film 17 by using the moisture supplying element 21 just after the sensor 10 is manufactured so that the maximum amount of moisture in the humidity sensitive film 17 becomes the upper limit, i.e., the sensor characteristics becomes the standard characteristics H.

Before the sensor 10 detects the humidity, the sensor characteristics are returned to the standard characteristics H. For example, in a case where the sensor 10 is mounted on an automotive vehicle, the moisture is added into the humidity sensitive film 17 by using the moisture supplying element 21 when a driver turns on the start switch 31 such as an ignition switch. Thus, the maximum amount of moisture in the humidity sensitive film 17 is returned to the upper limit or approximately upper limit, i.e., the sensor characteristics are returned to the standard characteristics H.

Thus, just after the start switch 31 turns on, the sensor characteristics are changed to the standard characteristics H within a short time. Thus, on the basis of the standard characteristics H, which is initially set, the sensor 10 detects the humidity.

Accordingly, even when the humidity sensitive film 17 preliminarily absorbs the moisture, the sensor characteristics are returned to the standard characteristics H. Thus, the sensor characteristics are highly reproducible so that the sensor 10 detects the humidity with high accuracy. Specifically, the influence of deviation of the sensor characteristics from the initial characteristics M is eliminated.

Further, when the moisture in the atmosphere is high, the moisture may be condensed so that a water drop is formed on the humidity sensitive film 17. In this case, the moisture supply element 21 stops to supply the moisture to the humidity sensitive film 17, and the heater 13 heats the humidity sensitive film 17 so that the water drop is removed from the humidity sensitive film 17. Thus, the sensor characteristics are returned to the standard characteristics H so that the sensor 10 can detects the humidity accurately.

The moisture may be added to the humidity sensitive film 17 at a certain timing other than a switch-on operation and a switch-off operation. For example, when an interval between the latest switch-off operation and the successive switch-on operation is within 6 hours, the moisture is not added to the humidity sensitive film 17 even when the start switch 31 is turned on.

Alternatively, the driver or a passenger of the vehicle may operate a switch for the moisture supply element 21. In this case, for example, the driver switches on the moisture supply element 21 so that the moisture is added to the humidity sensitive film 17.

In the above sensor 10, the moisture is added to the humidity sensitive film 17 by using the moisture supplying element 21, so that the maximum amount of moisture in the humidity sensitive film 17 is set to be the upper limit or approximately upper limit of the maximum amount of moisture, which is initially set as the standard characteristics.

Accordingly, before detection of the humidity, the sensor has the standard characteristics H with high reproducibility. Thus, the influence of deviation of the sensor characteristics from the initial characteristics M is eliminated. Further, the detection accuracy of the humidity is improved.

(Modifications)

The detection electrode 15 may provide a heater. In this case, the detection electrode 15 is used for not only the electrode but also the heater. Accordingly, there is no need to form the heater 13 and the second insulation film 14. Thus, a manufacturing cost and a manufacturing process is reduced and simplified.

Alternatively, the sensor 10 may include an air blower such as a dryer for blowing warm wind to the humidity sensitive film 17. The air blower is disposed near the sensor 10, so that the moisture in the humidity sensitive film 17 is removed. Thus, the maximum amount of moisture returns to the standard maximum amount of moisture. In this case, there is no need to form the heater 13 in the sensor 10. The moisture in the humidity sensitive film 17 is eliminated from the film 17 by using a simple means such as the air blower.

The sensor 10 may have a magnetron for generating a high frequency wave having a frequency of, for example, 2.4 GHz. The magnetron is disposed near the humidity sensitive film 17 so that the moisture in the humidity sensitive film 17 is reduced by resonating the film 17 with the magnetron. Thus, the sensor characteristics are returned to the standard sensor characteristics L having the lower limit of the maximum amount of moisture or to be a value near the lower limit. In this case, the moisture in the humidity sensitive film 17 is removed for a comparative short time, compared with a case where the moisture is removed by the heater 13.

The sensor 10 may include the heater 13 and the moisture supplying element 21. In this case, the standard sensor characteristics L, H are preliminarily obtained, and the user such as the driver and/or the passenger of the vehicle can select the sensor characteristics as the upper limit of the maximum amount of moisture H or the lower limit of the maximum amount of moisture L.

When the standard sensor characteristics are set to be the lower limit of the maximum amount of moisture L, the deviation of sensor characteristics is small in a case where the sensor 10 is used in a dry condition. When the standard sensor characteristics are set to be the upper limit of the maximum amount of moisture H, the deviation of sensor characteristics is small in a case where the sensor 10 is used in a wet condition.

Thus, the user of the vehicle determines the environmental condition of the sensor 10, and then, the user selects the lower limit of the maximum amount of moisture L and the heater 13 when the sensor 10 is used in a dry condition. Further, the user selects the upper limit of the maximum amount of moisture H and the moisture supplying element 21 when the sensor 10 is used in a wet condition.

In the above case, there is no need to set the sensor characteristics preliminary, so that the sensor 10 has high system generality.

Here, a selector for selecting the sensor characteristics may be disposed in the sensor 10. Specifically, when the user inputs a command for selecting the lower limit of the maximum amount of moisture L, the sensor automatically selects the heater 13. When the user inputs a command for selecting the upper limit of the maximum amount of moisture H, the sensor automatically selects the moisture supplying element 21.

The heater 13 and the moisture supplying element 21 provide a returning means, and the humidity sensitive film 17 provides a humidity sensitive member. Specifically, the heater 13 provides a heating means, and the moisture supplying element 21 provides a moisture supplying means.

The above disclosure has the following aspects.

According to an aspect of the present disclosure, a humidity sensor includes: a substrate; a pair of electrodes arranged on the substrate in such a manner that the electrodes are separated each other by a predetermined distance therebetween; a humidity sensitive member disposed between the electrodes, wherein the humidity sensitive member has a capacitance, which is changeable in accordance with humidity; an output element connecting to the electrodes in order to detect a capacitance of the humidity sensitive member and outputting a signal corresponding to the capacitance; and a setting member for setting a maximum amount of moisture in the humidity sensitive member to be a standard maximum amount of moisture. The humidity sensitive member is capable of absorbing a moisture up to the maximum amount of moisture. The setting member includes at least one of an element for reducing the maximum amount of moisture and an element for increasing the maximum amount of moisture.

In the above sensor, before detection of the humidity, the sensor characteristics reproducibly return to the standard characteristics so that detection accuracy of the sensor is improved.

Alternatively, the standard maximum amount of moisture may be a lower limit of the maximum amount of moisture or an approximately lower limit of the maximum amount of moisture. Further, the setting member may be a heater for heating the humidity sensitive member so that the maximum amount of moisture is set to the standard maximum amount of moisture. In this case, by controlling a heating condition such as a heating time, the lower limit of the maximum amount of moisture is controlled. For example, the heating time for reaching the lower limit of the maximum amount of moisture is preliminarily determined. Then, the heater heats the humidity sensitive film for a predetermined time equal to or longer than the preliminarily determined heating time. Thus, the standard maximum amount of moisture surely becomes the lower limit of the maximum amount of moisture.

Alternatively, the standard maximum amount of moisture may be an upper limit of the maximum amount of moisture or an approximately upper limit of the maximum amount of moisture. Further, the setting member may be a moisture supplying element for supplying the moisture to the humidity sensitive member so that the maximum amount of moisture is set to the standard maximum amount of moisture. In this case, by controlling a moisture supplying condition such as a supplying time, the upper limit of the maximum amount of moisture is controlled. For example, the supplying time for reaching the upper limit of the maximum amount of moisture is preliminarily determined. Then, the moisture supplying element supplies the moisture to the humidity sensitive film for a predetermined time equal to or longer than the preliminarily determined supplying time. Thus, the standard maximum amount of moisture surely becomes the upper limit of the maximum amount of moisture.

Alternatively, each electrode may have a comb-teeth portion so that the comb-teeth portions of the electrodes are interleaved each other. Further, the setting member may be a heater for heating the humidity sensitive member so that the standard maximum amount of moisture is set to a lower limit of the maximum amount of moisture or an approximately lower limit of the maximum amount of moisture, and the heater has a meander shape so that the comb-teeth portion of each electrode overlaps with the meander shape of the heater. Furthermore, the heater, the electrode and the humidity sensitive member may be stacked on the substrate in this order.

Further, the setting member may be a moisture supplying element for supplying the moisture to the humidity sensitive member so that the standard maximum amount of moisture is set to an upper limit of the maximum amount of moisture or an approximately upper limit of the maximum amount of moisture, and the setting member is disposed over the humidity sensitive film. Furthermore, the sensor may further include: a heater for heating the humidity sensitive member. The heater has a meander shape so that the comb-teeth portion of each electrode overlaps with the meander shape of the heater, and the heater, the electrode and the humidity sensitive member are stacked on the substrate in this order.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A humidity sensor comprising:
    a substrate;
    a pair of electrodes arranged on the substrate in such a manner that the electrodes are separated each other by a predetermined distance therebetween;
    a humidity sensitive member disposed between the electrodes, wherein the humidity sensitive member has a capacitance, which is changeable in accordance with humidity;
    an output element connecting to the electrodes in order to detect a capacitance of the humidity sensitive member and outputting a signal corresponding to the capacitance; and
    a setting member for setting a maximum amount of moisture in the humidity sensitive member to be a standard maximum amount of moisture, wherein
    the humidity sensitive member is capable of absorbing a moisture up to the maximum amount of moisture,
    the setting member includes at least one of an element for reducing the maximum amount of moisture and an element for increasing the maximum amount of moisture,
    the sensor is mounted in an automotive vehicle, and
    the setting member sets the maximum amount of moisture to be the standard maximum amount of moisture when a start switch of the vehicle turns on.

2. A humidity sensor comprising:
    a substrate;
    a pair of electrodes arranged on the substrate in such a manner that the electrodes are separated each other by a predetermined distance therebetween;
    a humidity sensitive member disposed between the electrodes, wherein the humidity sensitive member has a capacitance, which is changeable in accordance with humidity;
    an output element connecting to the electrodes in order to detect a capacitance of the humidity sensitive member and outputting a signal corresponding to the capacitance; and
    a setting member for setting a maximum amount of moisture in the humidity sensitive member to be a standard maximum amount of moisture, wherein
    the humidity sensitive member is capable of absorbing a moisture up to the maximum amount of moisture,
    the setting member includes at least one of an element for reducing the maximum amount of moisture and an element for increasing the maximum amount of moisture,
    the sensor is mounted in an automotive vehicle, and
    the setting member sets the maximum amount of moisture to be the standard maximum amount of moisture when a start switch of the vehicle turns off.

3. The sensor according to claim 1, wherein
    the standard maximum amount of moisture is a lower limit of the maximum amount of moisture or an approximately lower limit of the maximum amount of moisture.

4. The sensor according to claim 3, wherein
the element for reducing the maximum amount of moisture is a heater for heating the humidity sensitive member so that the maximum amount of moisture is set to the standard maximum amount of moisture.

5. The sensor according to claim 1, wherein
the standard maximum amount of moisture is an upper limit of the maximum amount of moisture or an approximately upper limit of the maximum amount of moisture.

6. The sensor according to claim 5, wherein
the element for increasing the maximum amount of moisture is a moisture supplying element for supplying the moisture to the humidity sensitive member so that the maximum amount of moisture is set to the standard maximum amount of moisture.

7. The sensor according to claim 6, further comprising:
a heater for heating the humidity sensitive member.

8. The sensor according to claim 1, wherein
the humidity sensitive member is made of poly imide.

9. The sensor according to claim 1, wherein
each electrode has a comb-teeth portion so that the comb-teeth portions of the electrodes are interleaved each other.

10. The sensor according to claim 9, wherein
the setting member is a heater for heating the humidity sensitive member so that the standard maximum amount of moisture is set to a lower limit of the maximum amount of moisture or an approximately lower limit of the maximum amount of moisture, and
the beater has a meander shape so that the comb-teeth portion of each electrode overlaps with the meander shape of the heater.

11. The sensor according to claim 10, wherein
the heater, the electrode and the humidity sensitive member arc stacked on the substrate in this order.

12. The sensor according to claim 9, wherein
the setting member is a moisture supplying element for supplying the moisture to the humidity sensitive member so that the standard maximum amount of moisture is set to an upper limit of the maximum amount of moisture or an approximately upper limit of the maximum amount of moisture, and
the setting member is disposed over the humidity sensitive film.

13. The sensor according to claim 12, further comprising:
a heater for heating the humidity sensitive member, wherein
the heater has a meander shape so that the comb-teeth portion of each electrode overlaps with the meander shape of the heater, and
the heater, the electrode and the humidity sensitive member are stacked on the substrate in this order.

* * * * *